(12) United States Patent
Wendland et al.

(10) Patent No.: US 12,083,326 B2
(45) Date of Patent: Sep. 10, 2024

(54) DRUG DELIVERY DEVICE WITH RESTRICTED CAP REPLACEMENT

(71) Applicant: Sanofi-Aventis Deutschland GMBH, Frankfurt am Main (DE)

(72) Inventors: Stefan Wendland, Frankfurt am Main (DE); Michael Harms, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 122 days.

(21) Appl. No.: 17/527,748

(22) Filed: Nov. 16, 2021

(65) Prior Publication Data

US 2022/0072239 A1  Mar. 10, 2022

Related U.S. Application Data

(63) Continuation of application No. 16/322,362, filed as application No. PCT/EP2017/069134 on Jul. 28, 2017, now Pat. No. 11,185,640.

(30) Foreign Application Priority Data

Aug. 2, 2016 (EP) .................................... 16182303

(51) Int. Cl.
*A61M 5/32* (2006.01)
*A61M 5/31* (2006.01)
*A61M 5/50* (2006.01)

(52) U.S. Cl.
CPC ........ *A61M 5/3213* (2013.01); *A61M 5/3202* (2013.01); *A61M 5/3219* (2013.01); *A61M 5/50* (2013.01); *A61M 2005/312* (2013.01); *A61M 2005/3217* (2013.01); *A61M 2205/273* (2013.01)

(58) Field of Classification Search
CPC .............. A61M 5/3213; A61M 5/3202; A61M 5/3219; A61M 5/50; A61M 2005/312; A61M 2205/273
See application file for complete search history.

(56) References Cited

U.S. PATENT DOCUMENTS

| | | | |
|---|---|---|---|
| 3,101,841 A | 8/1963 | Baldwin | |
| 4,300,678 A | 11/1981 | Gyure et al. | |
| 4,571,242 A | 2/1986 | Klein et al. | |
| 5,312,368 A * | 5/1994 | Haynes | A61M 5/3216 604/263 |
| 6,394,983 B1 | 5/2002 | Mayoral et al. | |
| 8,945,067 B2 | 2/2015 | McLoughlin et al. | |
| 9,242,050 B2 | 1/2016 | Abry | |
| 2008/0097310 A1 | 4/2008 | Buehler et al. | |

(Continued)

FOREIGN PATENT DOCUMENTS

| CN | 1279619 | 1/2001 |
|---|---|---|
| CN | 101102804 | 1/2008 |

(Continued)

OTHER PUBLICATIONS

International Preliminary Report on Patentability in Appln. No. PCT/EP2017/069134, dated Feb. 5, 2019, 9 pages.

(Continued)

*Primary Examiner* — Bradley J Osinski
(74) *Attorney, Agent, or Firm* — Fish & Richardson P.C.

(57) ABSTRACT

The present disclosure relates to a drug delivery device that has a housing and a cap. The drug delivery device also has a lock that prevents the cap being fully replaced on the housing after the cap has been removed.

20 Claims, 11 Drawing Sheets

(56) References Cited

U.S. PATENT DOCUMENTS

| | | | |
|---|---|---|---|
| 2009/0200191 A1 | 8/2009 | Matsuda et al. | |
| 2009/0264829 A1* | 10/2009 | Harris | A61M 5/3202 |
| | | | 604/416 |
| 2010/0268169 A1* | 10/2010 | Llewellyn-Hyde | |
| | | | A61M 5/5086 |
| | | | 604/192 |
| 2013/0281938 A1 | 10/2013 | Ekman et al. | |
| 2014/0358078 A1* | 12/2014 | Fischer | A61M 5/50 |
| | | | 604/111 |

FOREIGN PATENT DOCUMENTS

| | | |
|---|---|---|
| CN | 101115458 | 1/2008 |
| EP | 0555974 | 8/1993 |
| EP | 2883563 | 6/2015 |
| JP | H5-337182 | 12/1993 |
| JP | 2014-502889 | 2/2014 |
| JP | 2015-523900 | 8/2015 |
| WO | WO 1999/026680 | 6/1999 |
| WO | WO 2006/064231 | 6/2006 |
| WO | WO 2009/040603 | 4/2009 |
| WO | WO 2011/047298 | 4/2011 |
| WO | WO 2012/085034 | 6/2012 |
| WO | WO 2013/192328 | 12/2013 |
| WO | WO 2014/144096 | 9/2014 |

OTHER PUBLICATIONS

International Search Report and Written Opinion in Appln. No. PCT/EP2017/069134, dated Oct. 19, 2017, 12 pages.

* cited by examiner

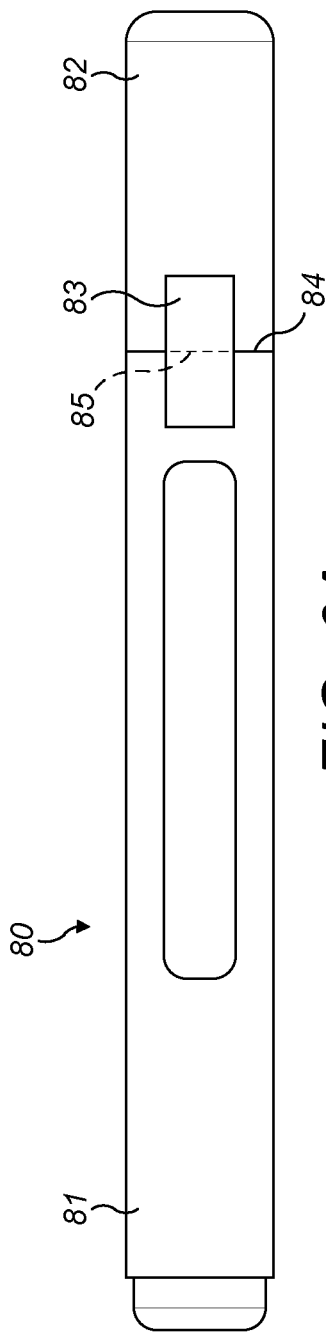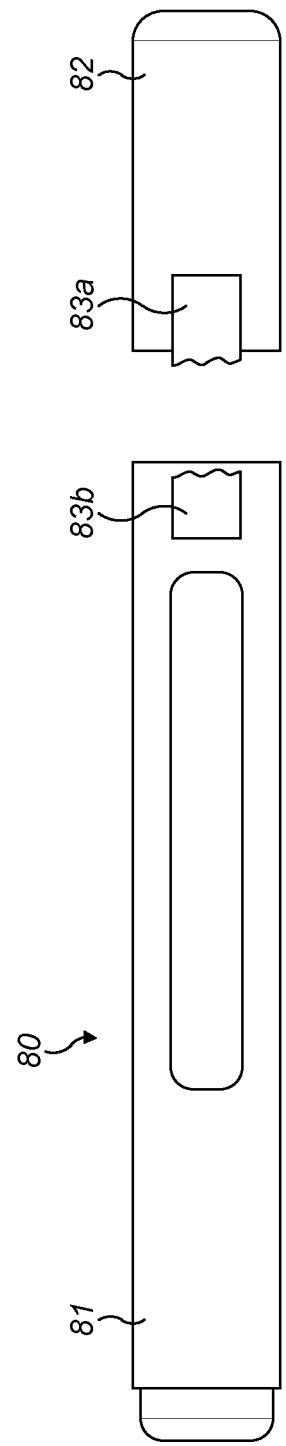
FIG. 6A
FIG. 6B

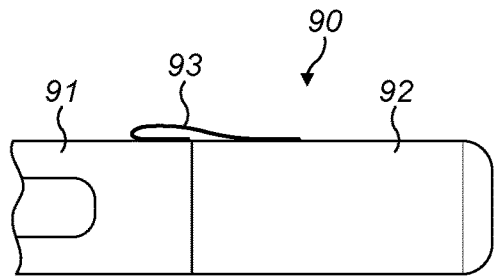
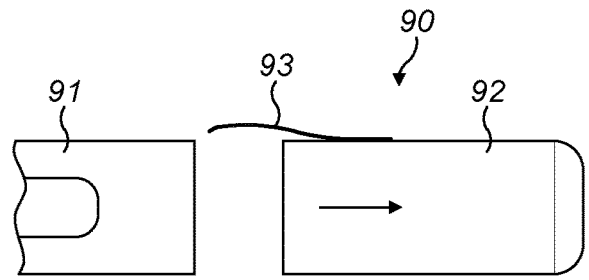
FIG. 7A  FIG. 7B
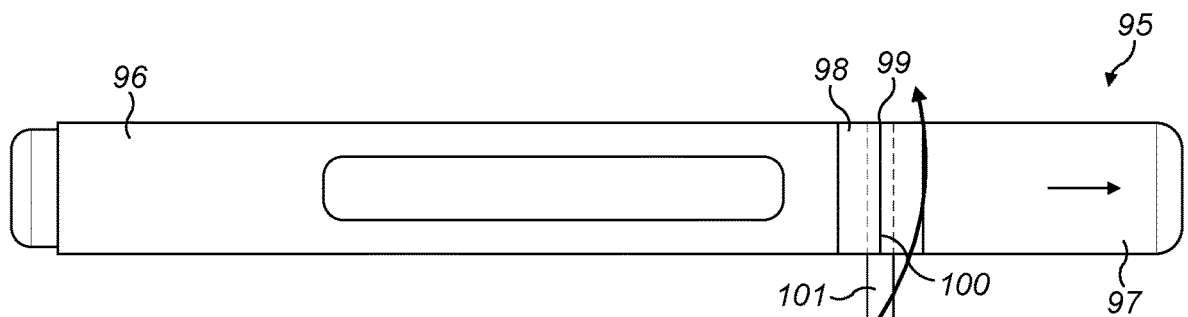
FIG. 8
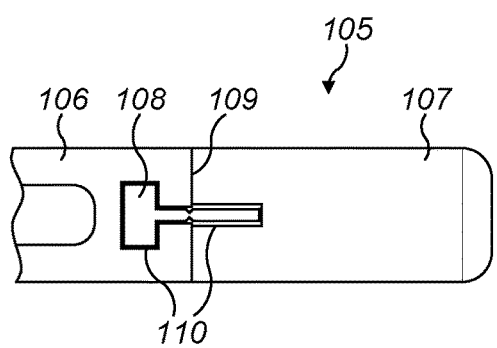
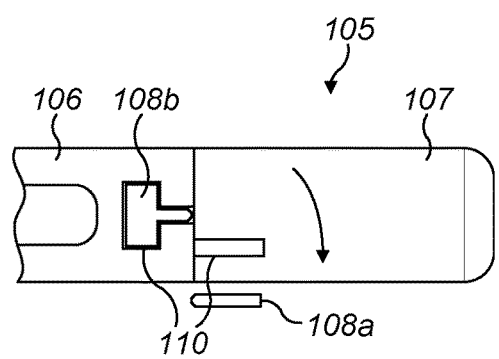
FIG. 9A  FIG. 9B

DRUG DELIVERY DEVICE WITH RESTRICTED CAP REPLACEMENT

CROSS REFERENCE TO RELATED APPLICATIONS

The present application is a continuation application of U.S. patent application Ser. No. 16/322,362, filed on Jan. 31, 2019, which is the national stage entry of International Patent Application No. PCT/EP2017/069134, filed on Jul. 28, 2017, and claims priority to Application No. EP 16182303.4, filed on Aug. 2, 2016, the disclosures of which are incorporated herein by reference.

TECHNICAL FIELD

The present disclosure relates to a drug delivery device, and to packaging for a drug delivery device.

BACKGROUND

Injector devices, such as auto-injectors, are known for dispensing medicament to an injection site of a patient. Such injection devices typically comprise a syringe having a needle, and a removable cap that covers the needle prior to use. Injection devices are typically provided in tamper-evident packaging that provides with a visual indication of prior use.

It is known to provide tear-open packaging for injector devices that cannot be reused. It is also known to package injector devices in blister packages that cannot be reused.

SUMMARY

In certain aspects, a drug delivery device is provided.

According to some embodiments, a drug delivery device comprising a housing, a cap, and a lock that prevents the cap being fully replaced on the housing after the cap has been removed is provided.

The lock may comprise a locking member configured to move into a locking position on first removal of the cap from the housing. The locking member may prevent the cap being fully replaced on the housing when the locking member is in the locking position.

The locking member may comprise a resiliently biased member.

The locking member may comprise a pre-stressed element.

The locking member may be in a deflected position and pushing against a part of the housing prior to first removal of the cap from the housing.

The locking member may be integral to the cap or the housing. In one example, the locking member may be integral to the cap and push against a part of the housing prior to first removal of the cap from the housing. In another example, the locking member may be integral to the housing and push against a part of the cap prior to first removal of the cap from the housing.

The locking member may comprise a spring. The spring may be mounted in the cap.

The cap and the housing may be arranged such that, prior to removal of the cap from the housing, the cap and the housing overlap in an overlapping region, and wherein the locking member may be disposed in the overlapping region.

The cap may comprise a cylindrical portion that at least partially surrounds a portion of the housing. In this example, the cylindrical portion of the cap may comprise at least two slots that define the locking member.

In some examples, the housing may comprise a needle for delivery of a drug, and the cap may cover the needle and may be removable.

The housing may comprise an indicium that is revealed on removal of the cap from the housing.

The indicium may be located such that the cap cannot be replaced on the housing in such a way as to cover the indicium.

The cap may comprise first and second parts that are assembled together on the housing.

The drug delivery device may further comprise packaging that includes a recess in which the drug delivery device is received, and wherein after first removal of the cap from the housing, a combined length of the housing and partially replaced cap is greater than a length of the recess to prevent the drug delivery device being replaced in the recess.

In some examples, there is provided a drug delivery device comprising:
 a housing comprising a needle for delivery of a drug;
 a removable cap that covers the needle; and
 a lock comprising a locking member that prevents the cap being fully replaced on the housing after the cap has been removed;
 wherein the locking member comprises a resiliently biased member that is held in a deflected position prior to first removal of the cap from the housing; and
 wherein the locking member is configured to move into a locking position on first removal of the cap from the housing, and wherein the locking member prevents the cap being fully replaced on the housing when the locking member is in the locking position.

According to a further aspect of the present invention, there is also provided a cap for a drug delivery device, said drug delivery device comprising a housing on which the cap can be received prior to use of said drug delivery device, the cap comprising a lock that prevents the cap being fully replaced on said housing after the cap has been removed.

According to a further aspect of the present invention, there is also provided a drug delivery device, the drug delivery device having a housing adapted to receive a cap prior to use of the drug delivery device, and wherein the drug delivery device comprises a lock that prevents said cap being fully replaced on the housing after said cap has been removed.

The drug delivery device may further comprise a reservoir of liquid medicament.

According to a further aspect of the present invention, there is also provided a method of using a drug delivery device, the method comprising removing a cap from a housing of said drug delivery device, and moving a lock to prevent said cap being fully replaced on said housing.

Also provided is packaging for a drug delivery device. The packaging comprises a recess arranged to hold a drug delivery device, and a tamper evident feature configured to provide an indication that the drug delivery device has been removed from the recess.

In another example, the packaging includes a recess arranged to hold a drug delivery device, and a tamper evident feature configured to prevent the drug delivery device being replaced in the recess after the drug delivery device has been removed from the recess.

In various examples, the packaging may include any one or more of: tabs that are broken on removing the drug delivery device from the recess; tabs that are delaminated on removing the drug delivery device from the recess; and/or, a locking member that prevents the drug delivery device being replaced in the recess after first removal of the drug delivery device from the recess. Such a locking member may be resiliently deformable.

In other examples provided herein, a drug delivery device has a housing and a removable cap. A closure line is defined between the housing and the removable cap when the cap is received on the housing. The drug delivery device may also have a tamper evident tab that extends across the closure line and is broken or removed from at least one of the housing and cap on first removal of the cap from the housing. For example, the tamper evident tab may be torn, peeled, delaminated, or snapped.

These and other aspects of the invention will be apparent from and elucidated with reference to the embodiments described hereinafter.

BRIEF DESCRIPTION OF THE DRAWINGS

Embodiments of the invention will now be described, by way of example only, with reference to the accompanying drawings, in which:

FIG. 6A is a top view of an injector device before the cap has been removed;

FIG. 6B is a top view of the injector device of FIG. 6A after the cap has been removed;

FIG. 7A is a top view of an injector device before the cap has been removed;

FIG. 7B is a top view of the injector device of FIG. 6A after the cap has been removed;

FIG. 8 is a top view of an injector device;

FIG. 9A is a top view of an injector device before the cap has been removed;

FIG. 9B is a top view of the injector device of FIG. 6A after the cap has been removed;

DETAILED DESCRIPTION

Figure 1A:
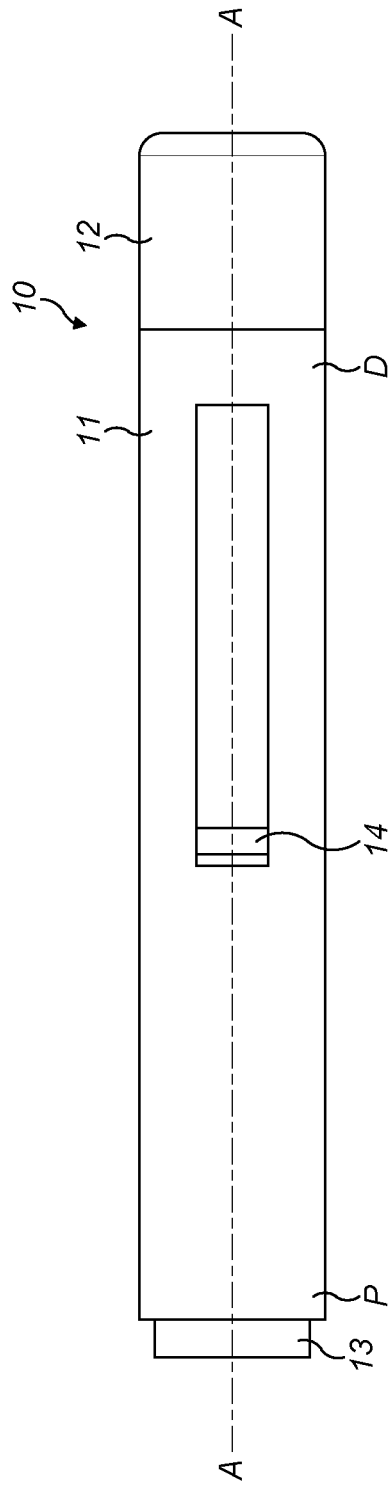
FIG. 1A is a schematic side view of an injector device, and a removable cap.

A drug delivery device, as described herein, may be configured to inject a medicament into a patient. For example, delivery could be sub-cutaneous, intra-muscular, or intravenous. Such a device could be operated by a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., about 3 to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 3 cP to about 50 cP. Consequently, a drug delivery device will often include a hollow needle ranging from about 25 to about 31 Gauge in size. Common sizes are 17 and 29 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

Figure 1B:
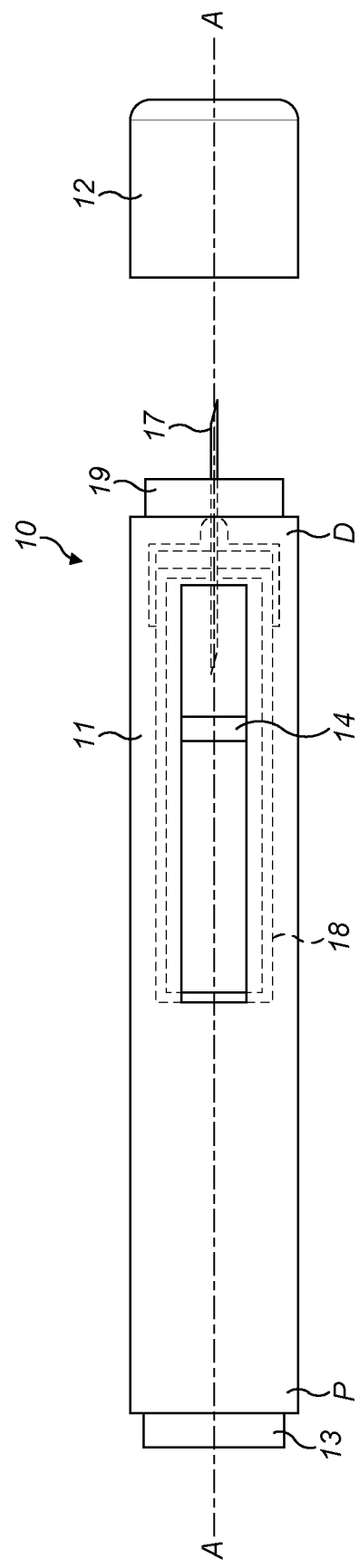
FIG. 1B is a schematic side view of the injector device of FIG. 1A, with the cap removed from the housing.

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a reservoir containing the medicament to be injected (e.g., a syringe) and the components required to facilitate one or more steps of the delivery process. A cap 12 is also provided that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung or piston 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of piston 14. Following activation, at least part of the energy stored in the drive spring can be applied to the proximal surface of piston 14. This compressive force can act on piston 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

Figure 2A:
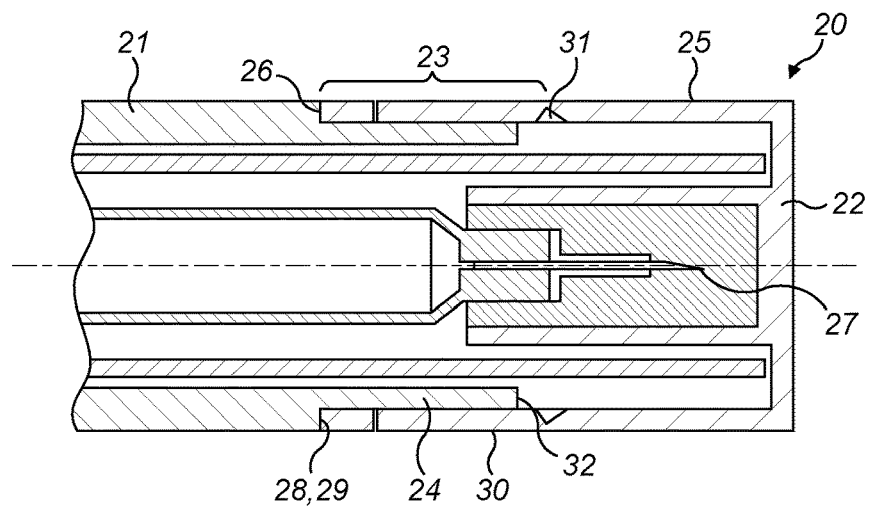
FIG. 2A is a cross-sectional view of an injector device in the region of the cap, with the cap being received on the housing.
Figure 2B:
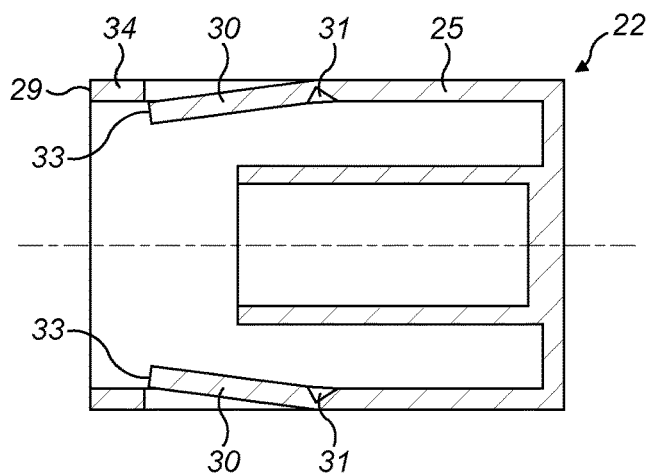
FIG. 2B is a cross-sectional view of the cap of FIG. 2A once removed from the housing.
Figure 2C:
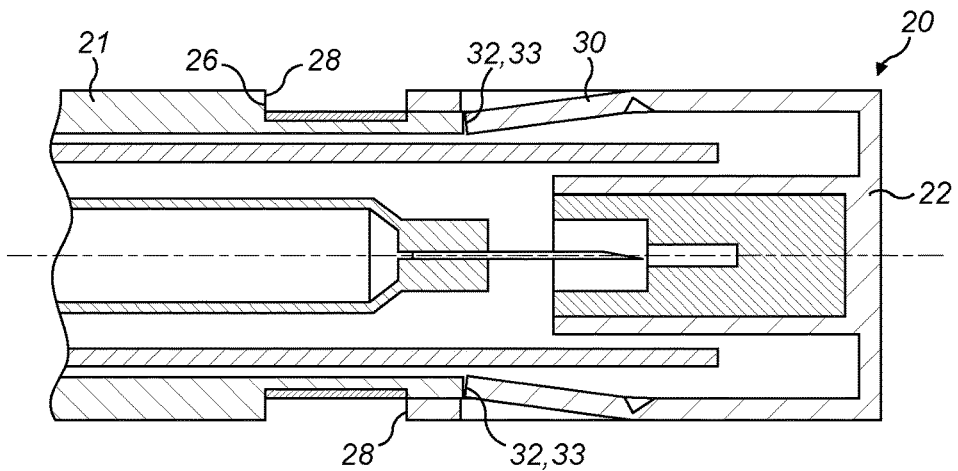
FIG. 2C is a cross-section view of the injector device of FIG. 2B, the cap being partially replaced on the housing.

FIGS. 2A, 2B and 2C show an example of an injector device 20 having a housing 21 with a removable cap 22. In this example, the cap 22 includes an integral tamper evident feature, in particular a lock that prevents the cap 22 being replaced on the housing 21 of the injector device 20. In this example, the injector device 20 has a needle 27 that is covered by the cap 22.

As shown in FIG. 2A, the cap 22 and the housing 21 overlap in an overlapping region 23. In particular, a distal portion of the housing 21 of the injector device comprises a cylindrical protrusion 24 that at least partially surrounds the needle 27, and the cap 22 comprises a cylindrical portion 25 that can be placed over the cylindrical protrusion 24 of the housing 21. In this example, the housing 21 comprises a shoulder 26 defining an annular surface 28 against which an end face 29 of the cap 22 abuts. However, it will be appreciated that the cap 22 may alternatively or additionally have such a shoulder, or there may be no shoulder so that the end face 29 of the cap 22 does not abut against a surface of the housing 21.

The cap 22 includes a locking member 30, which extends into the overlapping region 23. The locking member 30 is formed in the cylindrical portion 25 of the cap 22. In particular, the locking member 30 is defined by slots (not shown) within the cylindrical portion 25, and the locking member 30 has a hinge 31. The hinge 31 is formed by a notch in the wall of the cap 22.

The locking member 30 is pre-stressed towards a position in which it is deflected inwards relative to the cylindrical portion 25 of the cap 22. The locking member 30 may be moulded in the inwardly deflected portion, for example injection moulded, and thus would pre-stressed towards the deflected position.

The cylindrical portion 25 of the cap 22 may have one locking member 30, or may alternatively have two locking members 30. Preferably, the cap 22 has three locking members 30. The locking members 30 may be evenly spaced about the circumference of the cap 22. Two diametrically opposed locking members 30 are shown in FIG. 2A.

In this example, the locking members 30 are resiliently deformable, such that they can be deflected or deformed but will move back to their original position when not subject to any force.

In other examples, the locking members 30 may include embedded or adhered resilient elements, for example a spring.

In the closed position, shown in FIG. 2A, the locking members 30 are held outwards by the underlying cylindrical protrusion 24 of the housing 21. After the cap 22 is removed, as shown in FIG. 2B, the locking members 30 of the cap 22 deflect inwards, thereby preventing the cap 22 from being fully replaced on the housing, as shown in FIG. 2C. In particular, the locking members 30 abut the annular end face 32 of the cylindrical protrusion 24 on the housing 21 and prevent further insertion of the cylindrical protrusion 24 of the housing 21 into the cylindrical portion 25 of the cap 22.

In an alternative example, the locking members 30 may abut against another part of the housing 21 that prevents complete replacement of the cap 22 on the housing 21.

Also shown in FIGS. 2A and 2B, ends 33 of the locking members 30 are offset from the end face 29 of the cap 22. In this way, the cap 22 comprises a distal ring 34, and the ends 33 of the locking members 30 are offset from this distal ring 34, thereby preventing a user from easily grasping the locking members 30, which might otherwise allow a user to deform the locking members 30 in such a way that the cap 22 can be replaced on the housing 21.

An assembly tool may be used to first assemble the cap 22 and the housing 21. The assembly tool serving to hold the locking members 30 outwards to allow the cap 22 to be placed on the housing 21. Alternatively, the cap 22 may comprise two parts that are attached to each other and the housing 21 simultaneously. The two parts may be attached, joined or fastened together, for example through snap-fit features, fasteners (screws) or adhesive.

As the cap 22 cannot be replaced on the housing 21, there is no way to return the injector device 20 to its original state, and it is therefore clear that injector device 20 has been previously used (or at least opened).

FIGS. 3A, 3B, 3C and 3D show an injector device 40 similar to the injector device 30 of FIGS. 2A, 2B and 2C. Similar reference numerals are used for simplicity. In particular, the cap 42 has a cylindrical portion 45 that overlies a cylindrical protrusion 44 of the housing 41 of the injector device 40. However, in this example, a spring member 55 is located between the cap 42 and the housing 41 in the overlapping region 43. The spring member 55 is resiliently deformable and presses against the cylindrical protrusion 44 of the housing 41 in the overlapping region 43 when the cap 42 is in the closed position shown in FIG. 3A.

Figure 3A:
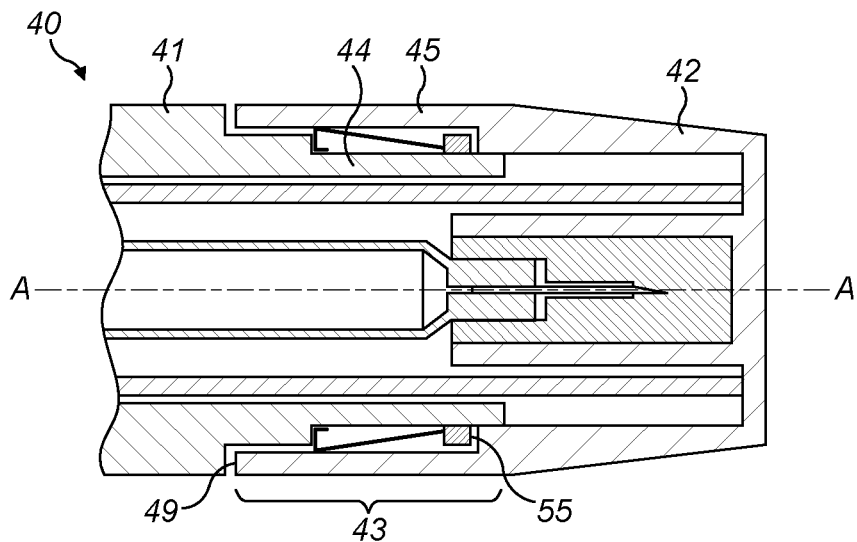
FIG. 3A is a cross-sectional view of an injector device in the region of the cap, with the cap being received on the housing.
Figure 3B:
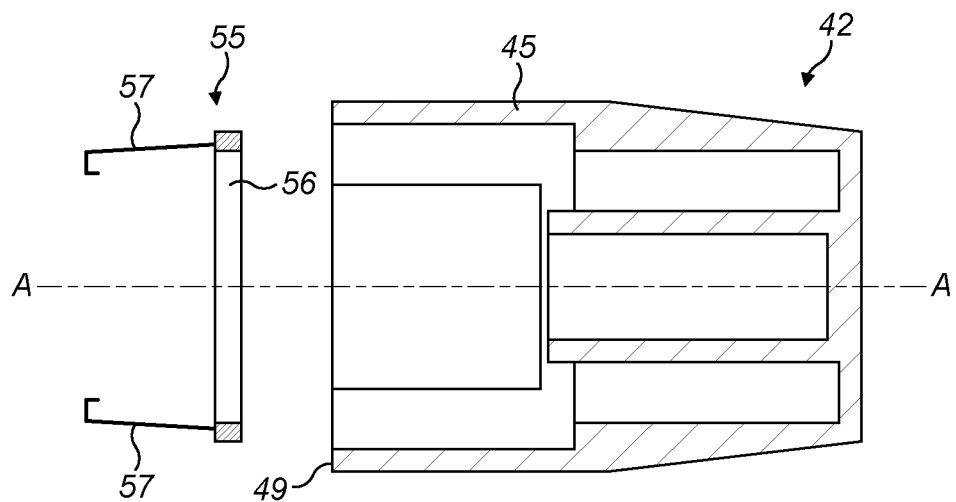
FIG. 3B is an exploded cross-sectional view of the cap and spring member of FIG. 3A.

As shown in FIG. 3B, the spring member 55 comprises a ring portion 56 and at least one arm 57 protruding from the ring portion 56. Preferably, the spring member 55 has more than one arm 57 protruding from the ring portion 56, most preferably three arms 57. FIG. 3B shows the cap 22 and spring member 55 separately.

The arms 57 are resiliently deformable and their natural position is deflected inwards towards the longitudinal axis A-A of the housing 41 and cap 22.

Figure 3C:
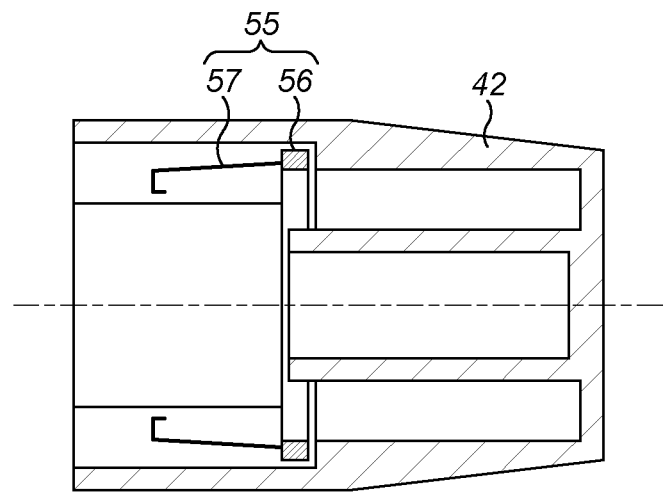
FIG. 3C is a cross-section view of the cap and spring member of FIG. 3A.
Figure 3D:
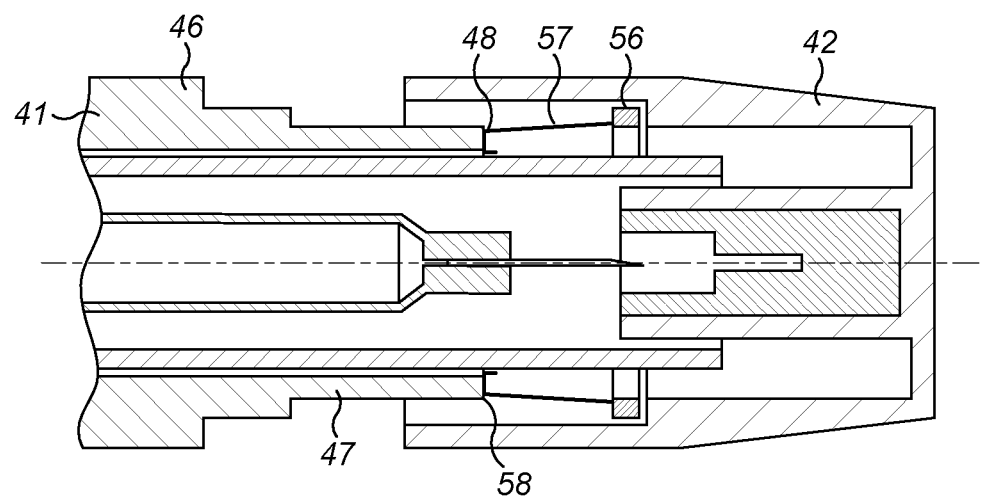
FIG. 3D is a cross-section view of the injector device of FIG. 3A, the cap being partially replaced on the housing.

As shown in FIG. 3A, which shows the cap 42 on the housing 41, in the closed position the arms 57 of the spring member 55 push against the cylindrical protrusion 44 of the housing 41. After the cap 42 has been removed from the housing 41 the arms 57 of the spring member 55 are released and move to their natural position, as shown in FIG. 3C. In this way, if a user attempted to replace the cap 42 on the housing 41 the arms 57 of the spring member 55 will abut against the end face 58 of the cylindrical protrusion 44 and prevent the cap 42 from being fully replaced on the housing 41, as shown in FIG. 3D.

In an alternative example, the arms 57 of the spring member 55 may abut against the annular face 48 of the shoulder 46 on the cylindrical protrusion 44 of the housing 41, or against another part of the housing 41 that prevents complete replacement of the cap 42 on the housing 41.

Also shown in FIGS. 3A and 3C, the ends of the arms 57 of the spring member 55 are offset from the end of the cylindrical portion 45 of the cap 42. That is, the arms 57 are entirely contained with the cap 42. In this way, a user is prevented from easily grasping the arms 57 of the spring member 55, which might otherwise allow a user to deform the arms 57 in such a way that the cap 42 can be replaced on the housing 41.

To assemble the cap 42, spring member 55 and housing 41 shown in FIG. 3A, the spring member 55 is first placed over the cylindrical protrusion 44 of the housing 41, and the cap 42 is then pushed onto the housing 41. The spring member 55 is thereby attached to the cap 42 by a snap-fit connection, clip, or press fit, so that when the cap 42 is removed from the housing 41 the spring member 55 is carried with the cap 42, the arms 57 deflect inwards, and the cap 42 is prevented from being replaced on the housing 41.

As the cap 42 cannot be replaced on the housing 41, there is no way to return the injector device to its original state, and it is therefore clear that injector device has been previously used (or at least opened).

Figure 4:
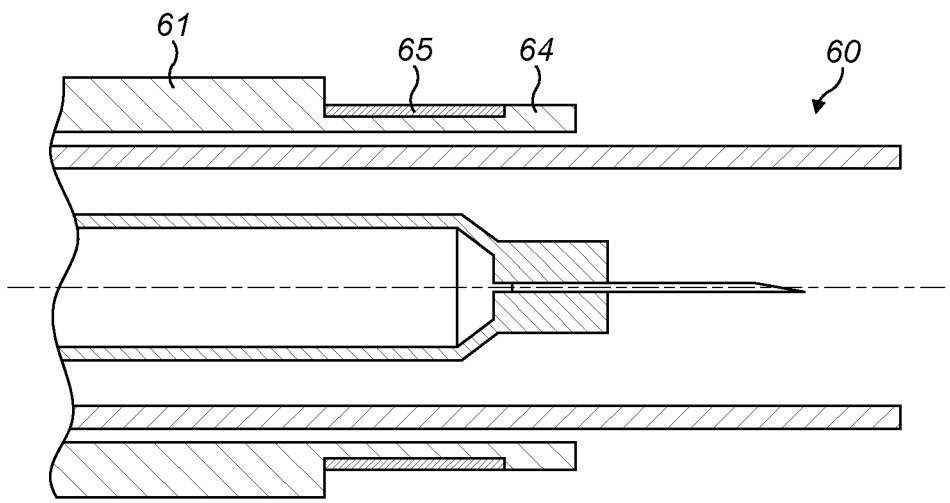
FIG. 4 is a cross-sectional view of an end of the housing of the injector device of FIGS. 3A and 3C.

FIG. 4 shows an example injector device 60 having a housing 61 that can be used with the caps 22, 42 of FIGS. 2A to 3D. In this example, a region 65 of the cylindrical protrusion 64 of the housing 61 may comprise indicia to indicate that the cap (not shown) has been removed and cannot be replaced. This region 65 of the housing 61 is only visible after removing the cap. In one example, the region 65 has text written on it, for example 'DEVICE PREVIOUSLY USED' OR 'DO NOT REPLACE CAP', or words to similar effect. Additionally or alternatively, the region 65 may be coloured, for example red, to indicate that the injector device 60 has been used previously. The region 65 is provided with indicia, and in this example indicia is intended to cover any visually distinct indicator that provides information to the user.

As illustrated in FIGS. 2C and 3D, once removed the cap 22, 42, cannot be completely replaced on the housing 21, 41, and the region 65 on the housing 61 is visible even if the cap 22, 42 is pushed partially back onto the housing 61.

In the examples of FIGS. 2A to 3D, the cap 22, 42 comprises a lock. In the example of FIGS. 2A to 2C, the lock is the locking members 30 that deflect inwards when the cap 22 is removed from the housing 21 to prevent the cap 22 being replaced on the housing 21. In the example of FIGS. 3A to 3D, the lock is the arms 57 of the spring member 55 that deflect inwards when the cap 42 is removed from the housing 41 to prevent the cap 42 being replaced on the housing 41.

In other examples, the lock may be provided on the housing 21, 41 instead of on the cap 22, 42. For example, the cylindrical protrusion 24, 44 of the housing 21, 41 may comprise locking members similar to those described with reference to FIGS. 2A to 2C, but in this example the locking members would be arranged to deflect outwards after the cap 22, 42 is removed and abut a part of the cap 22, 42 when attempting to replace the cap 22, 42 on the housing 21, 41.

Alternatively, a spring member similar to that described with reference to FIGS. 3A to 3D may be provided on the housing 21, 41, with arms arranged to deflect outwards on removal of the cap 22, 42 and abut a part of the cap 22, 42 when attempting to replace the cap 22, 42 on the housing 21, 41.

For example, the locking members or arms of the spring member provided on the housing 21, 41 may abut the end face 29, 49 of the cap 22, 42 to prevent replacement of the cap 22, 42 on the housing 21, 41.

As previously explained, and as shown in FIG. 2C and FIG. 3D, if a user attempts to replace the cap 22, 42 on the housing 21, 41 then the cap 22, 42 cannot be returned to its original position. Therefore, the combined length of the housing 21, 41 and cap 22, 42 is greater than the original combined length shown in FIG. 2A and FIG. 3A.

If the injector devices 10, 20, 40 described above were originally provided in further packaging then the further packaging can be designed such that the injector device 10, 20, 40, in particular the housing 11, 21, 41 and cap 12, 22, 42, cannot be replaced in the further packaging after the cap 12, 22, 42 has been removed from the housing 11, 21, 41.

Figure 5A:
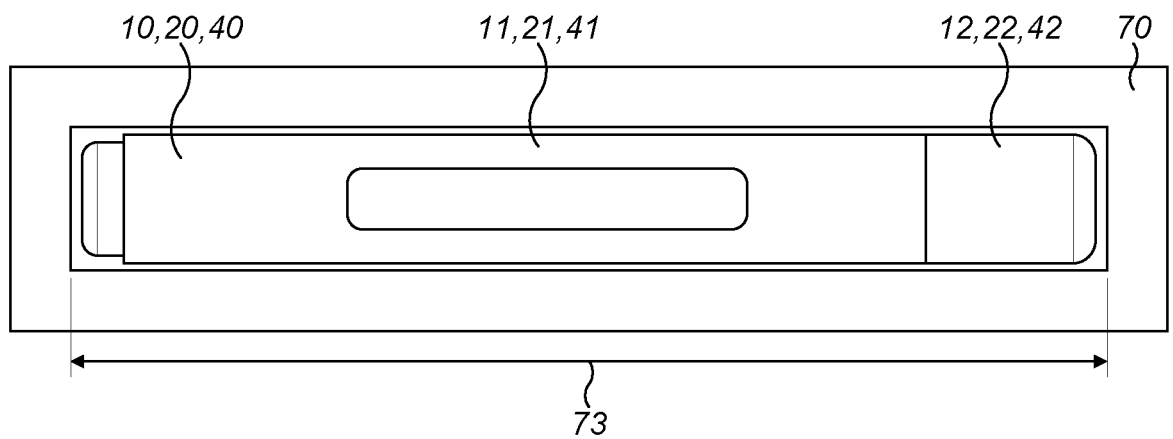
FIG. 5A is a top view of packaging for the injector device of FIGS. 1A to 4.
Figure 5B:
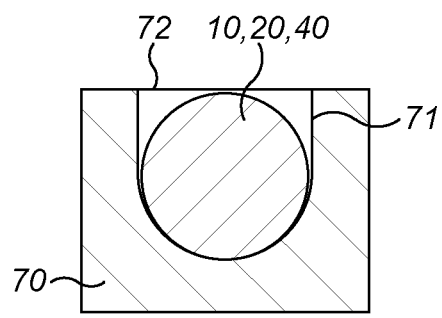
FIG. 5B is a cross-sectional end view of the packaging of FIG. 5A.

In one example, shown in FIGS. 5A and 5B, the further packaging 70 is a moulded plastic part that includes a recess 71 in which the injector device 10, 20, 40 received prior to use. A removable cover 72, for example a plastic film, may be provided over the recess 71 to seal the injector device 10, 20, 40 prior to use. As illustrated, the recess 71 is shaped to closely match the size and shape of the injector device 10, 20, 40. In particular, the length 73 of the recess 71 is approximately the same as, or slightly greater than, the length of the injector device 10, 20, 40.

In this way, the injector device 10, 20, 40 cannot be replaced in the recess 71 after the cap 22, 42 has first been removed because of the greater combined length of the housing 21, 41 and partially replaced cap 22, 42 (as shown in FIGS. 2C and 3D) exceeds the length 73 of the recess 71.

It will be appreciated that the injector devices 10, 20, 40 described in the examples of FIG. 2A to 5C may have different shapes. For example, they may alternatively have a square or hexagonal cross-sectional shape, instead of the circular cross-section shown in the figures and described above. Accordingly, other features of the injector device 10, 20, 40, in particular the housing 11, 21, 41 and cap 12, 22, 42, particularly the cylindrical protrusion 24, 44, 64 of the housing 21, 41 and the cylindrical portion 25, 45 of the cap 22, 42, may not be generally circular in shape, but may have another shape, for example square or hexagonal.

In addition, it will be appreciated that the injector devices 10, 20, 40 described with reference to any of FIG. 1A to FIG. 4 may be packaged, and the packaging may include tamper evident features. Examples of such tamper evident packaging are given hereinafter.

FIGS. 6A and 6B show an injector device 80 that includes a housing 81 and cap 82. The cap 82 covers a functional component of the injector device 80, for example a needle, and is removed before use of the injector device 80.

As shown in FIG. 6A, a tamper evident tab 83 extends across the closure line 84 between the housing 81 and the cap 82 and is attached to the housing 81 and the cap 82. As shown in FIG. 6B, the tamper evident tab 83 is broken into two parts 83a and 84 on removal of the cap 82 from the housing 81. Therefore, the broken tab 83a, 83b provides a visual indication that the cap 82 has previously been removed.

In various examples, the tamper evident tab 83 may include a line of weakness 85 where the tamper evident tab 83 is broken. The line of weakness 85 may be a thinning of the material, a line of perforations, a score line, or other line of weakness in the tamper evident tab 83. The tamper evident tab 83 may comprise paper, foil, plastics, or other material.

The tamper evident tab 83 may be attached to the housing 81 and the cap 82 by adhesive, welding (for example ultrasonic welding), heat sealing, or other attachment, also taking into account the materials used.

In a further example, the tamper evident tab 83 is formed from lacquer or wax that is cracked and broken on removing the cap 82 from the housing 81. For example, an ultraviolet lacquer may be applied to an area extending across the closure line 84 between the cap 82 and the housing 81 and allowed to cure.

FIGS. 7A and 7B show a further example injector device 90 having a housing 91, cap 92 and tamper evident tab 93. In this example, the tamper evident tab 93 is looped such that a first side of the tamper evident tab 93 is attached to the cap 92, and an opposite side of the tamper evident tab 93 is attached to the housing 91. In this way, as illustrated in FIG. 7B, as the cap 92 is removed from the housing 91 the tamper evident tab 93 is peeled off of the housing 91 and carried with the cap 92.

In a further example, a part of the tamper evident tab 93 may delaminate as the tamper evident tab 93 is peeled from the housing 91, such that a part of the tamper evident tab 93 remains on the housing 91 after removal of the cap 92. The remaining part of the tamper evident tab 93 may be coloured, or have indicia, to indicate that the cap 92 has been removed.

In other examples the loop of the tamper evident tab 93 is oppositely arranged, so that the tamper evident tab 93 is peeled off of the cap 92 and remains attached to the housing 91 on removal of the cap 92. In this example, the tamper evident tab 93 may have a delaminating part that remains attached to the cap 92.

The tamper evident tab 93 may be attached to the housing 91 and the cap 92 by adhesive, welding (for example ultrasonic welding), heat sealing, or other attachment, also taking into account the materials used.

FIG. 8 shows a further example of an injector device 95 having a housing 96 and a cap 97. In this example, a sealing ring 98 surrounds the closure line 99 between the housing 96 and the cap 97. The sealing ring 98 includes a tear strip 100 that has a pull flap 101. Pulling the pull flap 101 removes the tear strip 100 from the sealing ring 98 and separates the sealing ring 98 into two parts at the closure line 99, one part being on each of the housing 96 and the cap 97. This allows the cap 97 to be separated from the housing 96.

The sealing ring 98 may be attached to both the housing 96 and the cap 97, or may be tightly wrapped or shrink-wrapped about the closure line 99 so that the cap 97 cannot be removed without first removing the tear strip 100. The sealing ring 98 may be attached to the housing 96 and the cap 97 by adhesive, welding (for example ultrasonic welding), heat sealing, or other attachment, also taking into account the materials used.

The tear strip 100 may be formed by a line of perforations in the sealing ring 98, or it may include an additional strip of material that is adhered to the sealing ring 98 and which propagates a tear through the sealing ring 98.

FIGS. 9A and 9B show a further example of an injector device 105 having a housing 106 and a cap 107. In this example, the cap 107 is removed by twisting the cap 107 relative to the housing 106. The cap 107 and housing 106 may include thread portions or engaging portions arranged such that the cap 107 cannot be pulled straight off, but must be at least partially rotated to release the thread portions or engaging portions before the cap 107 can be removed from the housing 106.

A tamper evident tab 108 is attached to both the housing 106 and the cap 107 and extends across the closure line 109 in a longitudinal direction of the injector device 105. In this way, the tamper evident tab 108 is broken into two parts 108*a*, 108*b* when the cap 107 is twisted, as shown in FIG. 9B.

The tamper evident tab 108 may be a paper, foil, plastics tab or a wax or lacquer. Preferably, the tamper evident tab 108 is a hard plastics member that is snapped when the cap 107 is twisted relative to the housing 106. The hard plastics member may include a weakened region that breaks on twisting the cap 107.

The tamper evident tab 108 may be attached to the housing 106 and the cap 107 by adhesive, welding (for example ultrasonic welding), heat sealing, or other attachment, also taking into account the materials used. Alternatively, the tamper evident tab 108 may be received in a recess 110 in the housing 106 and/or in the cap 107 in such a way that it cannot be removed unless the cap 107 is removed from the housing 106.

Figure 10A:
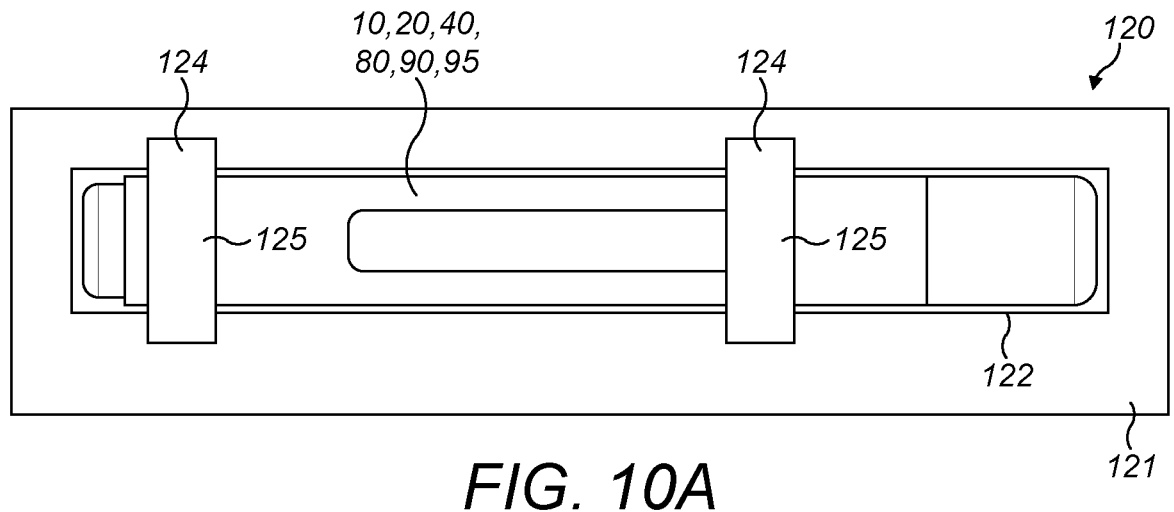
FIG. 10A is a top view of packaging for the injector device of FIGS. 1A to 4 and 6A to 9B, prior to first opening.
Figure 10B:
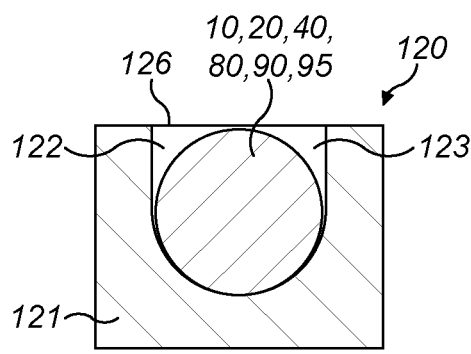
FIG. 10B is a cross-section end view of the packaging of FIG. 10A.

FIG. 10A shows an example of packaging 120 for the injector devices 10, 20, 40, 80, 90, 95, 105 described with reference to FIG. 1A to 9B. In particular, FIG. 10A shows a moulding 121 and an injector device 10, 20, 40, 80, 90, 95 received in the moulding 121. FIG. 10B shows a cross sectional end-view of the moulding 121 in the region of the injector device 10, 20, 40, 80, 90, 95. As shown in FIG. 10B, the moulding 121 has a recess 122 for the injector device 10, 20, 40, 80, 90, 95, the recess 122 being sized so that the injector device 10, 20, 40, 80, 90, 95 can be received in the recess 122. The size of the recess 122 is such that the injector device 10, 20, 40, 80, 90, 95 cannot move substantially within the recess 122, which protects the injector device 10, 20, 40, 80, 90, 95 against damage. The recess 122 also has an opening 123 for removal of the injector device 10, 20, 40, 80, 90, 95 from the moulding 121.

It will be appreciated that the moulding 121 shown in FIG. 10A may have a single recess 122, for packaging a single injector device, or two recesses 122 for packaging two injector devices. Alternatively, the moulding 121 may have any number of recesses 122 for injector devices, for example three, four or more recesses.

As shown in FIG. 10A and FIG. 10B, the packaging 120 also has tamper evident tabs 124 that extend across the opening 123 of the recess 122. In this example, there are two tamper evident tabs 124, but it will be appreciated that there may be any number of tamper evident tabs 124, for example one, three, or more.

The tamper evident tabs 124 are attached to the moulding 121 on either side of the recess 122.

The tamper evident tabs 124 may be attached to the moulding 121 by an adhesive, welding (e.g. ultrasonic welding), heat sealing, or any other attachment suitable for the particular materials of the moulding 121 and the tamper evident tabs 124.

The tamper evident tabs 124 are positioned such that the injector device 10, 20, 40, 80, 90, 95 cannot be removed from the recess 122 without breaking or detaching at least one of the tamper evident tabs 124. On removal of the injector device 10, 20, 40, 80, 90, 95 from the recess 122 at least one of the tamper evident tabs 124 is broken and/or detached from the moulding 121, as shown in FIG. 10C.

In one example, each tamper evident tab 124 has a foil section 125 extending over the recess 122 that is broken on removing the injector device 10, 20, 40, 80, 90, 95 from the recess 122. In another example, each tamper evident tab 124 comprises paper. In another example, each tamper evident tab 124 comprises a plastic material, for example a plastic film.

In some examples the tamper evident tab 124 is broken, for example torn, on removal of the injector device 10, 20, 40, 80, 90, 95 from the recess 122. In other examples, one side of the tamper evident tab 124 is detached from the moulding 121 on removal of the injector device 10, 20, 40, 80, 90, 95 from the recess 122. In another example, each tamper evident tab 124 detaches from both sides of the recess 122 on removal of the injector device 10, 20, 40, 80, 90, 95 from the recess 122. In other examples, a part of the tamper evident tab 124 is arranged to delaminate as the tamper evident tab 124 is detached from the moulding 121, thereby leaving a visual indication of previous removal of the injector device 10, 20, 40, 80, 90, 95. The delaminated part of the tamper evident tab 124 may be coloured, or have indicia, that informs the user that the tamper evident tab 124 has been broken and thereby indicate that the injector device 10, 20, 40, 80, 90, 95 has previously been removed from the recess 122.

Figure 10C:
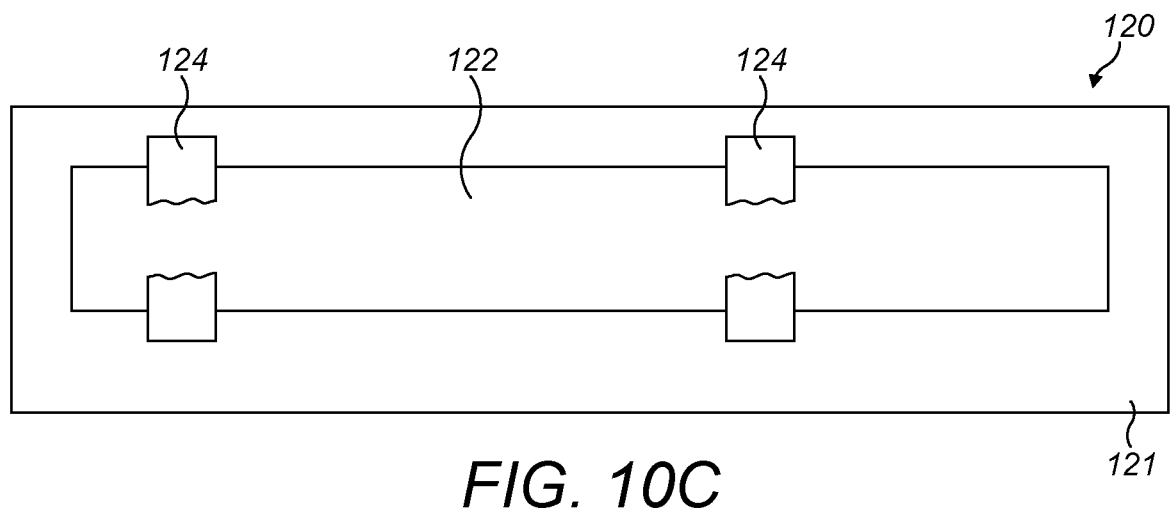
FIG. 10C is a top view of the packaging of FIGS. 10A and 10B after the injector device has been removed.

FIG. 10C shows the packaging 120 after removal of the injector device 10, 20, 40, 80, 90, 95. In this example, the tamper evident tabs 124 have been broken by removing the injector device 10, 20, 40, 80, 90, 95 from the recess 122. Therefore, if the injector device 10, 20, 40, 80, 90, 95 were replaced in the recess 122 there is a visual indication that the injector device 10, 20, 40, 80, 90, 95 has been removed from the packaging 120 previously.

The injector device 10, 20, 40, 80, 90, 95 is placed in the recess 122 during manufacture, particularly during packaging. The tamper evident tabs 124 may be attached to the moulding 121 so that they extend over the opening 123 of the recess 122 after the injector device 10, 20, 40, 80, 90, 95 has been placed in the recess 122.

The packaging 120 may additionally include a cover 126 over the recess, as shown in FIG. 10B, for example a plastic film that is peeled off before removing the injector device 10, 20, 40, 80, 90, 95 from the recess 122. The tamper evident tabs 124 may be an integral part of the cover 126, or the tamper evident tabs 124 may be additional to the cover 126.

Figure 11A:
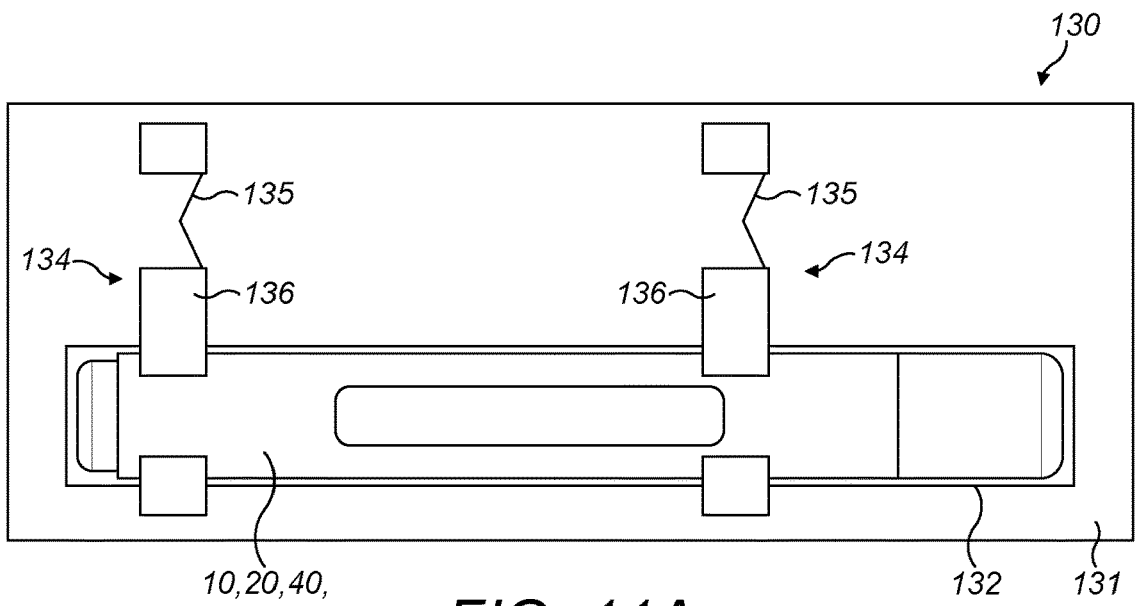
FIG. 11A is a top view of packaging for the injector device of FIGS. 1A to 4 and 6A to 9B, prior to first opening.
Figure 11B:
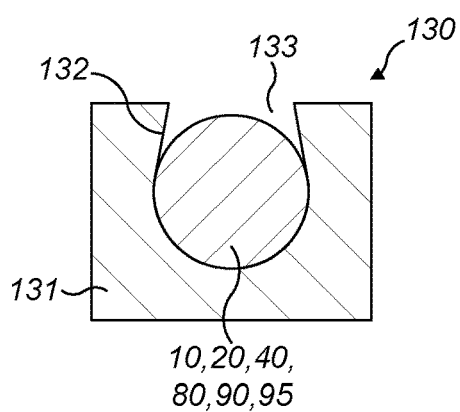
FIG. 11B is a cross-section end view of the packaging of FIG. 11A, prior to the injector device being removed.

FIG. 11A shows a further example of packaging 130 for the injector devices 10, 20, 40, 80, 90, 95 described with reference to FIG. 1A to 9B. In this example, the packaging 130 has a moulding 131. The moulding 131 includes a recess 132 to receive an injector device 10, 20, 40, 80, 90, 95. FIG. 11B shows a cross-sectional end view of the moulding 131 with an injector device 10, 20, 40, 80, 90, 95 received in the recess 132, and FIG. 11C shows the moulding 131 after the injector device 10, 20, 40, 80, 90, 95 has been removed.

Figure 11C:
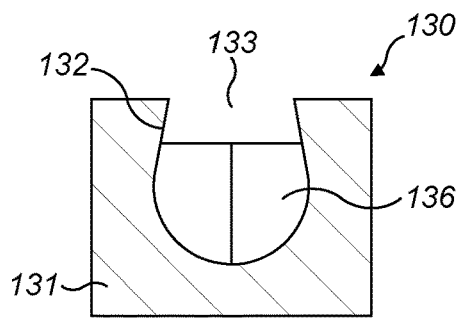
FIG. 11C is a cross-section end view of the packaging of FIG. 11A, after to the injector device has been removed.

As shown in FIGS. 11A, 11B and 11Cc, the recess 132 is sized so that the injector device 10, 20, 40, 80, 90, 95 can be received in the recess 132. The recess 132 also has an opening 133 through which the injector device 10, 20, 40, 80, 90, 95 can be removed from the moulding 131.

As shown in FIG. 11A, the packaging 130 includes a lock 134. The lock 134 comprises a resiliently deformable member 135 arranged to move a blocking member 136 into the recess 132 132 when the injector device 10, 20, 40, 80, 90, 95 is removed, to prevent the injector device 10, 20, 40, 80, 90, 95 being replaced in the recess 132. While the injector device 10, 20, 40, 80, 90, 95 is in the recess 132 the blocking member 136 is urged against the side of the injector device 10, 20, 40, 80, 90, 95. On removal of the injector device 10, 20, 40, 80, 90, 95 from the recess 132 the resiliently deformable member 135 moves the blocking member 136 into the recess, as shown in FIG. 11C, to prevent replacement of the injector device 10, 20, 40, 80, 90, 95 in the recess 132.

The blocking member 136 may be coloured, or be provided with indicia, to indicate that the packaging 130 has been used.

The example shown in FIG. 11A has two locks 134, but it will be appreciated that the packaging 130 may include one lock 134, or more than two locks 134, for example three or four or more locks 134.

It will be appreciated that the moulding 131 shown in FIG. 11A may have a more than one recess 132, for packaging multiple injector devices 10, 20, 40, 80, 90, 95. For example, the moulding 131 may have any number of recesses for injector devices 10, 20, 40, 80, 90, 95, for example two, three, four or more.

Figure 12A:
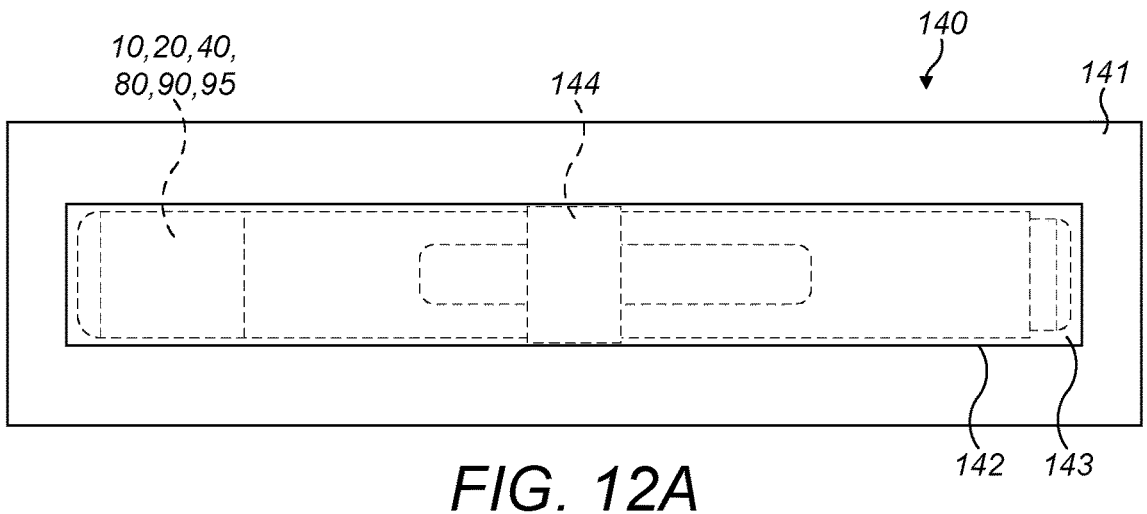
FIG. 12A is a is a top view of packaging for the injector device of FIGS. 1A to 4 and 6A to 9B, prior to first opening.
Figure 12B:
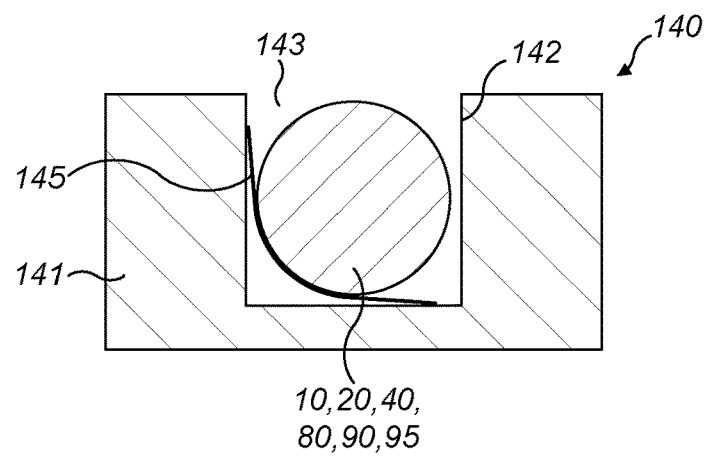
FIG. 12B is a cross-section end view of the packaging of FIG. 12A, prior to the injector device being removed.
Figure 12C:
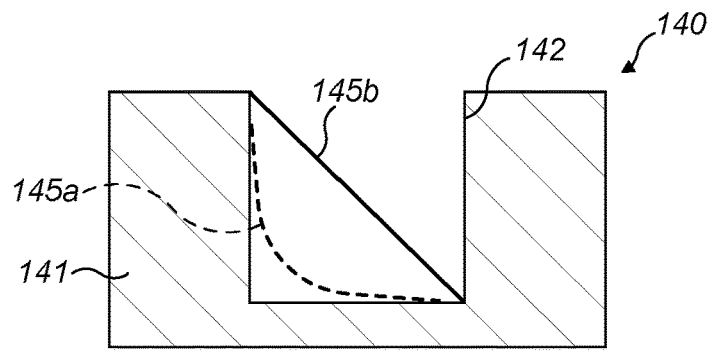
FIG. 12C is a cross-section end view of the packaging of FIG. 12A, after to the injector device has been removed.

FIGS. 12A, 12B and 12C show another example of packaging 140 for the injector devices 10, 20, 40, 80, 90, 95 described with reference to FIG. 1A to 9B. The packaging 140 includes a lock 144. In this example the packaging includes a moulding 141 having a recess 142 with an opening 143 through which an injector device 10, 20, 40, 80, 90, 95 is received, similar to the example of FIGS. 11A, 11B and 11C. In this example, the lock 144 comprises a resiliently deformable member 145 disposed within the recess 142.

As shown in FIG. 11B and FIG. 11C, the resiliently deformable member 145 has two positions, a deflected position 145a, and a blocking position 145b. When the injector device 10, 20, 40, 80, 90, 95 is positioned in the recess 142 the resiliently deformable member 145 is held in the deflected position 145a by the injector device 10, 20, 40, 80, 90, 95. On removal of the injector device 10, 20, 40, 80, 90, 95 from the recess 142 the resiliently deformable member 145 moves into the blocking position 145b and thereby prevents replacement of the injector device 10, 20, 40, 80, 90, 95 in the recess 142.

The natural position of the resiliently deformable member 145 is the blocking position 145b, so that the resiliently deformable member 145 moves from the deflected position 145a to the blocking position 145b automatically when the injector device 10, 20, 40, 80, 90, 95 is removed from the recess 142.

In an alternative example, a spring is located underneath the resiliently deformable member 145 and acts to urge the resiliently deformable member 145 from the deflected position 145a to the blocking position 145b when the injector device 10, 20, 40, 80, 90, 95 is removed from the recess 142.

It will be appreciated that the resiliently deformable member 145 may not be entirely located in the recess 142—it may extend into the recess 142 from a position outside of the recess 142.

In examples, the deformable member 145 moves from the deflected position 145a into a straightened position, as shown in FIG. 12C, or into a bent position such that it blocks replacement of the injector device 10, 20, 40, 80, 90, 95 in the recess 142.

Figure 13A:
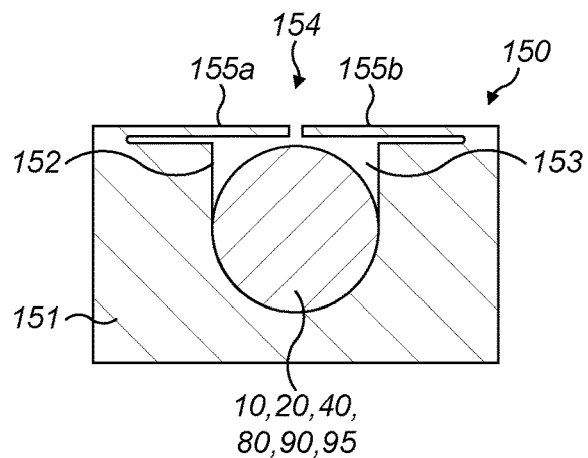
FIG. 13A is a cross-sectional end view of packaging for the injector device of FIGS. 1A to 4 and 6A to 9B, prior to the injector device being removed from the packaging.
Figure 13B:
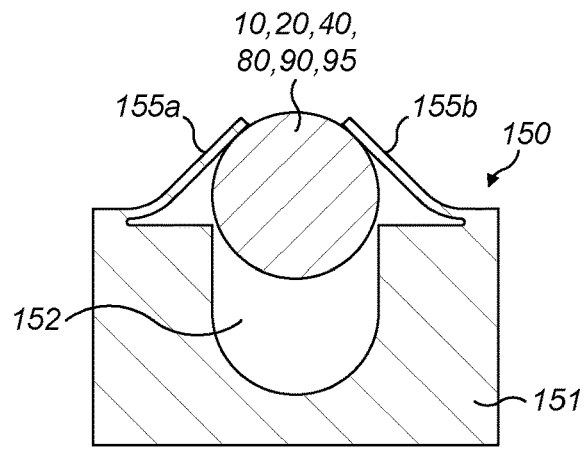
FIG. 13B is a cross-sectional end view of packaging of FIG. 13A during removal of the injector device from the packaging; and, FIG. 13C is a cross-sectional end view of packaging of FIG. 13A after the injector device has been removed from the packaging.
Figure 13C:
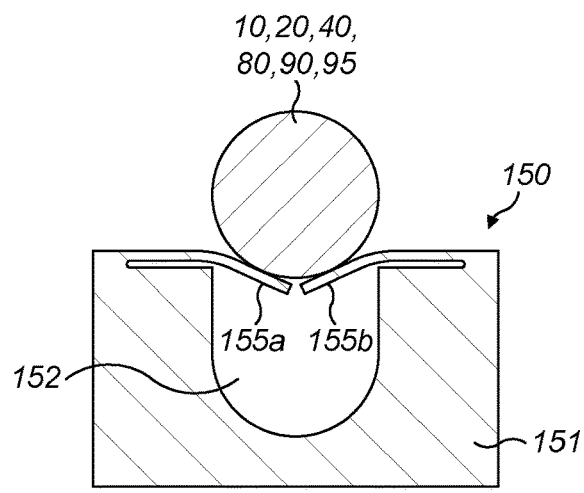

FIGS. 13A, 13B and 13C show a further example of packaging 150 for the injector devices 10, 20, 40, 80, 90, 95 described with reference to FIG. 1A to 9B. The packaging 150 has a moulding 151 that includes a recess 152 having an opening 153 through which the injector device 10, 20, 40, 80, 90, 95 can be removed from the packaging 150. The packaging 150 also includes a lock 154.

In this example, the lock 154 comprises a pair of flaps 155 arranged oppositely across the opening 153 of the recess 152. In particular, the lock 154 comprises a first flap 155a attached on a first side of the recess 152, and a second flap 155b on a second side of the recess 152. The first and second flaps 155a, 155b each extend towards each other, each extending partially across the opening 153 of the recess 152. In this example, as shown in FIG. 13A, the flaps 155a, 155b almost meet in the centre above the opening 153. However, in other examples the flaps 155a, 155b may be further spaced from each other, or they may be abutting, or they may be overlapping. In other examples, the flaps 155a, 155b may be different size.

As shown in FIG. 13A, before first use the flaps 155a, 155b hold the injector device 10, 20, 40, 80, 90, 95 in the recess 152. As shown in FIG. 13B, the flaps 155a, 155b are resiliently deformable such that the injector device 10, 20, 40, 80, 90, 95 can be removed from the recess 152 by pulling or levering the injector device 10, 20, 40, 80, 90, 95 such that the flaps 155a, 155b are deformed. However, as shown in FIG. 13C, the injector device 10, 20, 40, 80, 90, 95 cannot be replaced in the recess 152 because the flaps 155a, 155b are unable to deform in such a way to allow the injector device 10, 20, 40, 80, 90, 95 to pass underneath the flaps 155a, 155b and into the recess 152.

In particular, in the example the attachment between the flaps 155a, 155b and the moulding 151 is offset from the edge of the opening 153 of the recess 152. In this way, as the injector device 10, 20, 40, 80, 90, 95 is removed from the recess 152 the flaps 155a, 155b are able to pivot about the point of attachment between the flaps 155a, 155b and the moulding 151. On the other hand, on attempting to replace the injector device 10, 20, 40, 80, 90, 95 in the recess 152 the flaps 155a, 155b would have to pivot about fulcrums defined on the edges of the opening 153 of the recess 152, which permits less deformation of the flaps 155a, 155b, thereby preventing the injector device 10, 20, 40, 80, 90, 95 from being replaced in the recess 152.

The flaps 155a, 155b may be integral with the moulding 151, for example formed as part of the moulding 151. Alternatively, the flaps 155a, 155b may be attached to the moulding 151, for example by an adhesive, welding (for example ultrasonic welding), by heat sealing, or by any other attachment.

The flaps 155a, 155b may be made from a plastic material, a card material, a metal, or any other suitable material.

Each of the examples provides tamper evident packaging for an injector device. The tamper evidence is an indication of the packaging having been previously opened. In the above examples, the tamper evidence is, for example, a broken tamper evident tab, or a lock that prevents the injector device being repackaged. The advantage of providing tamper evidence packaging for injector devices is that the user, for example a patient, can quickly, easily and safely determine whether the injector device has been unpackaged previously, and can then dispose of the injector device if it has been unpackaged previously. This is beneficial for hygiene and medical safety reasons.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, or other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° ° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-gamma-glutamyl)-des(B30) human insulin; B29-N—(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a polysulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in certain aspects of the present invention include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. A drug delivery device comprising:
a housing configured to receive a needle; and
a cap removably attached to the housing to cover the needle;
wherein the cap comprises a locking member having a proximal end and a distal end, the locking member connected to the cap at the distal end of the locking member and extending proximally from a wall of the cap, the locking member comprising a resiliently biased member that is held in a deflected position when the cap is fully connected to the drug delivery device, and wherein the locking member is movable relative to the wall of the cap to a locking position when the cap is removed from the housing, the locking member in the locking position being configured to prevent the cap from being attached to the housing.

2. The drug delivery device of claim 1, wherein the proximal end of the locking member is a free end of the locking member.

3. The drug delivery device of claim 2, wherein the free end of the locking member comprises a proximally facing surface configured to, in the locking position of the locking member, abut a portion of the housing to prevent the cap from being attached to the housing.

4. The drug delivery device of claim 1, wherein the locking member is configured such that the locking member extends inwardly relative to the wall of the cap when the locking member is in the locking position.

5. The drug delivery device of claim 1, further comprising:
a hinge connecting the locking member to the cap,
wherein the locking member is movable about the hinge to the locking position.

6. The drug delivery device of claim 5, wherein the hinge is formed by a notch in the wall of the cap.

7. The drug delivery device of claim 1, wherein the locking member is resiliently biased toward the locking position.

8. The drug delivery device of claim 1, wherein the proximal end of the locking member is configured to push against the housing when the cap is removably attached to the housing.

9. The drug delivery device of claim 1, wherein the cap and the locking member are configured such that the wall of the cap, a wall of the housing, and the locking member are aligned along an axis parallel to a longitudinal axis of the drug delivery device when the cap is removably attached to the housing.

10. The drug delivery device of claim 1, wherein the cap comprises a cylindrical portion distal to the locking member, the cylindrical portion at least partially surrounding a portion of the housing.

11. The drug delivery device of claim 10, wherein the cap comprises a slot extending proximally from the cylindrical portion, the slot defining the locking member.

12. The drug delivery device of claim 1, wherein the housing comprises the needle.

13. The drug delivery device of claim 1, wherein the housing comprises an indicium configured to be revealed on removal of the cap from the housing.

14. The drug delivery device of claim 13, wherein the indicium is located such that the cap cannot be replaced on the housing in such a way as to cover the indicium.

15. A system comprising:
a drug delivery device comprising
a housing configured to receive a needle;
a cap removably attached to the housing to cover the needle;
wherein the cap comprises a locking member having a proximal end and a distal end, the locking member connected to the cap at the distal end of the locking member and extending proximally from a wall of the cap, the locking member comprising a resiliently biased member that is held in a deflected position when the cap is fully connected to the drug delivery device, and wherein the locking member is movable relative to the wall of the cap to a locking position when the cap is removed from the housing, the locking member in the locking position being configured to prevent the cap from being attached to the housing; and
packaging that comprises a recess in which the drug delivery device is received,
wherein the drug delivery device is configured such that after first removal of the cap from the housing, a combined length of the housing and the cap when the cap is partially replaced on the housing is greater than a length of the recess of the packaging to prevent the drug delivery device from being replaced in the recess of the packaging.

16. The drug delivery device of claim 1, further comprising a reservoir of liquid medicament.

17. A cap assembly for a drug delivery device, the cap assembly comprising:
a cap configured to be removably attached to the drug delivery device to cover a needle received by the drug delivery device;
wherein the cap comprises a locking member having a proximal end and a distal end, the locking member connected to the cap at the distal end of the locking member and extending proximally from a wall of the cap, the locking member comprising a resiliently biased member that is held in a deflected position when the cap is fully connected to the drug delivery device, and wherein the locking member is movable relative to the wall of the cap to a locking position when the cap is removed from the drug delivery device, the locking member in the locking position being configured to prevent the cap from being attached to the drug delivery device.

18. The cap assembly of claim 17, wherein the proximal end of the locking member is a free end of the locking member comprising a proximally facing surface configured to, in the locking position of the locking member, abut a portion of the drug delivery device to prevent the cap from being attached to the drug delivery device.

19. The cap assembly of claim 17, wherein:
the locking member is configured such that the locking member extends inwardly relative to the wall of the cap when the locking member is in the locking position, and
the cap and the locking member are configured such that the wall of the cap, a wall of the drug delivery device, and the locking member are aligned along an axis parallel to a longitudinal axis of the drug delivery device when the cap is removably attached to the drug delivery device.

20. The cap assembly of claim 17, wherein the cap comprises:
a cylindrical portion distal to the locking member, the cylindrical portion configured to at least partially surround a portion of the drug delivery device when the cap is removably attached to the drug delivery device; and
a slot extending proximally from the cylindrical portion, the slot defining the locking member.

* * * * *